US008609723B2

(12) United States Patent
Ku et al.

(10) Patent No.: US 8,609,723 B2
(45) Date of Patent: Dec. 17, 2013

(54) LONG ACTING CURCUMIN DERIVATIVE, PREPARATION METHOD AND PHARMACEUTICAL USE THEREOF

(75) Inventors: Baoshan Ku, Beijing (CN); Weidong Zhou, Beijing (CN); Fenghua Yu, Beijing (CN); Haiyan Yao, Beijing (CN); Guangyin Yao, Beijing (CN)

(73) Assignee: Beijing Dingguochangsheng Biotech., Co., Ltd., Beijing (CN)

( * ) Notice: Subject to any disclaimer, the term of this patent is extended or adjusted under 35 U.S.C. 154(b) by 209 days.

(21) Appl. No.: 13/062,940

(22) PCT Filed: Sep. 28, 2008

(86) PCT No.: PCT/CN2008/001688
§ 371 (c)(1),
(2), (4) Date: Mar. 8, 2011

(87) PCT Pub. No.: WO2010/025589
PCT Pub. Date: Mar. 11, 2010

(65) Prior Publication Data
US 2011/0183945 A1  Jul. 28, 2011

(30) Foreign Application Priority Data

Sep. 8, 2008 (CN) .......................... 2008 1 0222059
Sep. 8, 2008 (CN) .......................... 2008 1 0222060
Sep. 8, 2008 (CN) .......................... 2008 1 0222061

(51) Int. Cl.
*A01N 37/02* (2006.01)
*A01N 37/06* (2006.01)
*A61K 31/225* (2006.01)
*C07C 69/76* (2006.01)

(52) U.S. Cl.
USPC ......................................... 514/548; 560/104

(58) Field of Classification Search
USPC ............... 514/163, 546, 548; 560/106, 104
See application file for complete search history.

(56) References Cited

FOREIGN PATENT DOCUMENTS

| CN | 101076336 A | 11/2007 |
| CN | 101170915 A | 4/2008 |
| DE | 10245988 A1 * | 4/2004 |
| WO | WO 2004/031122 A1 | 4/2004 |

OTHER PUBLICATIONS

Dong et. al., Journal of Natural Products, 1998, American Chemical Society, vol. 61, pp. 142-144.*
Rai et. al., Nucleic Acids Symposium Series, Sep. 8, 2008, Oxford University Press, No. 52, pp. 599-600.*
Shah, Biotechnology: Pharmaceutical Aspects, 2007, Springer, vol. V, pp. 357-377.*
Chen, F. et al. 2007 "Review on curcuminoids separated from the *Curcuma* genus" *Journal of Guangxi Teachers Education University* (Natural Science Edition) 24(2):95-100.
Anand, P. et al. 2010 "Design of curcumin-loaded PLGA nanoparticles formulation with enhanced cellular uptake, and increased bioactivity in vitro and superior bioavailability in vivo" *Biochemical Pharmacology* 79:330-338.
Bhatia, N. et al. 2011 "Adaptogenic potential of curcumin in experimental chronic stress and chronic upredictable stress-induced memory deficits and alteration in functional homeostasis" *Journal National Medicine* Apr 11, 2011 [Epub ahead of print], (12 pages).
Bhutani, M. K. et al. 2009 "Anti-depressant like effect of curcumin and its combination with peperine in unpredictable chronic stress-induced behavioral, biochemical and neurochemical changes" *Pharmacology, Biochemistry and Behavior* 92:39-43.
Katsori, A.-M. et al. 2011 "Curcumin analogues as possible anti-proliferative & anti-inflammatory agents" *European Journal of Medicinal Chemistry* Apr 5. [Epub ahead of print], (14 pages).
Kunnumakkara, A.B. et al. 2008 "Curcumin inhibits proliferation, invasion, angiogenesis and metastasis of different cancers through interaction with multiple cell signaling proteins" *Cancer Lett* 269(2):199-225 (Epub May 13, 2008).
Kunwar, A. et al. 2008 "Quantitative cellular uptake, localization and cytotoxicity of curcumin in normal and tumor cells" *Biochimica et Biophysica Acta* 1780:673-679.
Lin, J.-K. 2007 "Molecular Targets of Curcumin" *Adv Exp Med Biol* 595: 227-243.
Pan, M.-H. et al. 1999 "Biotransformation of Curcumin Through Reduction and Glucuronidation in Mice" *Drug Metabolism and Disposition* 27:486-494.
Qian, H. et al. 2011 "Curcumin enhanced adriamycin-induced human liver-derived Hepatoma G2 cell death through activation of mitochondria-mediated apoptosis and autophagy" *Eur J Pharm Sci.* Apr 14, 2011 [Epub ahead of print], (7 pages).
Reuter, S. et al. 2007 "Modulation of anti-apoptotic and survival pathways by curcumin as a strategy to induce apoptosis in cancer cells" *Biochem Pharmacol* 76(11):1340-1351. Epub Aug 3, 2008.
Shishodia S. et al. 2007 "Role of Curcumin in Cancer Therapy" *Curr Probl Cancer* 31:243-305.
Wang, R. et al. 2008 "The antidepressant effects of curcumin in the forced swimming test involve 5-HT$_1$ and 5-HT$_2$ receptors" *European Journal of Pharmacology* 578:43-50.

(Continued)

*Primary Examiner* — Sarah Pihonak
(74) *Attorney, Agent, or Firm* — Knobbe, Martens, Olson & Bear, LLP

(57) ABSTRACT

The invention provides a long acting curcumin derivative, preparation method and pharmaceutical use thereof, wherein said long acting curcumin derivative having the general structural formula disclosed herein, wherein R1 and R2 are hydrogen or methoxyl; R3 and R4 are each independently selected from C1-C50 alkyl. Compared with cuminoids, the inventive long acting curcumin derivative has a better release effect, a higher bioavailability and pharmaceutical activity, and thus can be useful for the treatment of diseases such as depression and cancer.

9 Claims, 8 Drawing Sheets

(56) References Cited

OTHER PUBLICATIONS

Wang, R. et al. 2008 "Curcumin protects against glutamate excitotoxicity in rat cerebral cortical neurons by increasing brain-derived neurotrophic factor level and activating TrkB" *Brain Research* 1210: 84-91.

Xu, Y. et al. 2008 "Curcumin reverses the effects of chronic stress on behavior, the HPA axis, BDNF expression and phosphorylation of CREB" *Brain Research* 1122: 56-64.

Xu, Y. et al. 2009 "Curcumin reverses impaired cognition and neuronal plasticity induced by chronic stress" *Neuropharmacology* 57:463-471.

Xu, Y. et al. 2007 "Curcumin reverses impaired hippocampal neurogenesis and increases serotonin receptor 1A mRNA and brain-derived neurotrophic factor expression in chronically stressed rats" *Brain Research* 1162: 9-18.

Xu, Y. et al. 2005 "Antidepressant effects of curcumin in the forced swim test and olfactory bulbectomy models of depression in rats" *Pharmacology, Biochemistry and Behavior* 82:200-206.

Xu, Y. et al. 2005 "Antidepressant effect of curcumin in mice" *Chinese Journal of Clinical Rehabilitation* 9:162-164.

\* cited by examiner

A: control group  B: Long acting curcumin group  C: 5-Fu group

LONG ACTING CURCUMIN DERIVATIVE, PREPARATION METHOD AND PHARMACEUTICAL USE THEREOF

RELATED APPLICATIONS

This application is a U.S. National Phase of International Application No.: PCT/CN2008/001688, filed Sep. 28, 2008, designating the U.S. and published in English on Mar. 11, 2010 as WO 2010/025589 A1, which claims the benefit of Chinese Application No. 200810222061.7, filed Sep. 8, 2008, Chinese Application No. 200810222060.2, filed Sep. 8, 2008 and Chinese Application No. 200810222059.X, filed Sep. 8, 2008.

FIELD OF THE ART

The invention relates to a curcumin derivative, particularly a long acting curcumin derivative with an excellent slow-release effect, preparation method and pharmaceutical use thereof.

BACKGROUND OF THE ART

Curcuminoids (Cur), normally a mixture of curcumin, demethoxycurcumin and bisdemethoxycurcumin, are phenol-type pigments extracted from Chinese medicines *curcuma* and Aromatic Turmeric Root-tuber. Modern pharmacological investigations show that curcuminoids possess many pharmacological activity, such as anticancer, anti-inflammation, anti-oxidation, blood fat reduction, and anti-depression acitivties with little toxic and side effect.

Depression is a complicated mental disorder and its primary manifestations include low spirits, fewer speech, hypopsychosis and bradykinesia. The incidence of depression increases year by year. Additionally, depression is often concurrent with many other diseases and thus severely harms human health. The currently used anti-depression medicines in clinic generally function by impacting reabsorption of monoamine transmitter, inhibiting metabolism of monoamine, or blocking pre-synapse suppressive autonomous or non-autonomous receptors. Although these medicines all function well in the treatment of depression, many of them have no stable activity, but have a relatively large toxic and side effect. Therefore, development of safe and effective anti-depression medicines with little toxic and side effect from traditional Chinese herbal medicines has become the focus of investigation in this field.

A variety of medicines are currently available for the treatment of tumors. However, while exerting an anticancer function, each of these medicines also exhibits toxic effect to healthy histiocytes, and may cause some adverse reactions, such as secondary tumors, hepatic and renal toxicities and marrow suppression, alimentary tract reactions, and baldness etc. In contrast, curcumin has hitherto exhibited no significant toxic and side effect. Plenty of cellular experiments and animal experiments have indicated that curcumin has a clear-cut antitumor activity, a broader anticancer spectrum and less toxic and side effect, and thus becomes a novel anticancer medicine with a broad application prospect. Currently, curcumin has entered into a pre-clinical toxicological test stage.

*Curcuma* is the major ingredient in the Chinese medicine Compound Xiaoyao Powder. It has been reported that curcumin and its derivatives has an anti-depression effect in animal depression model. And it is known from the current documentations that curcumin has a function of treating various diseases without any toxic or side effect, and thus may be applied in a very broad field, which is mainly due to the activity of the polyphenol structure in curcumin. Concerning chemical structure, curcuminoids mainly include three substances: curcumin, demethoxycurcumin and bisdemethoxycurcumin. Their chemical structures are shown as follows:

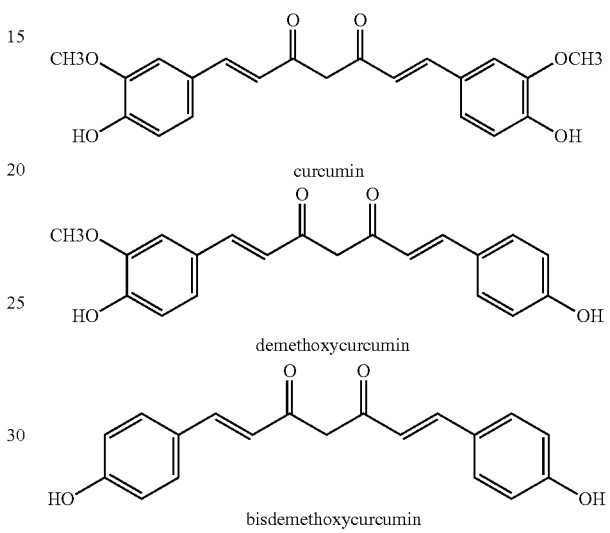

Fat is an essential component of human body, and mainly metabolized by β-oxidation after its absorption by human body. Curcumin has a very short half life, i.e. approximately 1 hour. In addition, all of current curcumin and its derivatives have low bioavailability, and poor water-solubility and ester-solubility.

In view of the above defects of current curcumin and its derivatives, the inventors, based on their abundant practice experience and professional knowledge in this field, intend to provide a long acting curcumin derivative, preparation method and pharmaceutical use thereof, so as to improve the drug activity and practicability of the current curcumin and its derivatives. After intensively hard work, the present invention with a practical value was completed.

DISCLOSURE OF THE INVENTION

The objective of the invention is to provide a novel long acting curcumin derivative, preparation method and pharmaceutical use thereof, so as to overcome the defects of the current curcumin and its derivatives. The technical problem to be solved is to improve ester-solubility, to extend action time, to reduce dosage while ensuring the safety and zero toxic and side effect, so as to impart the inventive curcumin derivatives with a better practicability.

The objective of the invention and technical problem to be solved in the invention are achieved by the following technical solutions. According to the invention, a long acting curcumin derivative with the following structure formula is provided:

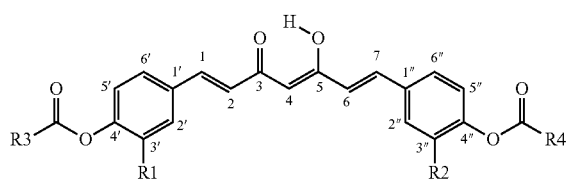

wherein:

R1 and R2 are hydrogen or methoxyl; R3 and R4 are each independently selected from C1-C50 alkyl, including linear or branched alkyl, such as ethyl, propyl, isopropyl, t-butyl and the like. R3 and R4 can also be independently selected from C1-C50 unsaturated aliphatic hydrocarbon including alkenyl, polyalkenyl, hydroxyl, polyhydroxyl and the like, or cyclic aromatic groups.

The objective of the invention and technical problem to be solved in the invention can be also achieved by way of the technical solutions shown as follows.

The long acting curcumin derivative as recited above, wherein the groups at 4', 4" C positions of the long acting curcumin derivative are esters generated from the esterification reactions independently occurring between C1-C50 saturated fatty acids or acylates thereof and the hydroxyl groups at 4', 4" C positions of cuminoids, respectively.

The long acting curcumin derivative as recited above, wherein the groups at 4', 4"C positions of the long acting curcumin derivative are esters generated from the esterification reactions independently occurring between C1-C50 unsaturated fatty acids or acylates thereof, or aromatic fatty acids or acylates thereof and the hydroxyl groups at 4', 4" C positions of cuminoids, respectively.

The long acting curcumin derivative as recited above, wherein the cuminoids are selected from curcumin, demethoxycurcumin or bisdemethoxycurcumin.

The long acting curcumin derivative as recited above, wherein the unsaturated fatty acids include palmitoleic acid, oleic acid, linoleic acid, linolenic acid, arachidonic acid, eicosapentaenoic acid (EPA) or docosahexenoic acid (DHA).

The long acting curcumin derivative as recited above, wherein said R3 and R4 are each independently selected from decyl, linoleate or salicylate.

The objective of the invention and technical problem to be solved in the invention can also be achieved by way of the technical solutions shown as follows. According to the invention, a method for the preparation of a long acting curcumin derivative is provided. Such a method comprises the steps of 1) weighing and dissolving 2~4 mmol cuminoids into dioxane, to which 0.3~0.73 g pyridine, and then 3.6~8.60 mmol C1-C50 saturated fatty acids, unsaturated fatty acids and aromatic fatty acids or acylates thereof are added dropwise, and allowing the system to react for 1~2 hours in an ice water bath; 2) pouring the product of step 1) into petroleum ether for filtering, dissolving the resultant precipitate in ethyl acetate, washing twice with 1 mol/L hydrochloric acid solution and then once with saturated sodium carbonate solution, drying the product by addition of anhydrous sodium sulfate, and filtering, spinning to remove the filtrate, and obtaining curcumin alkyl ester as crude product; and 3) loading said crude product onto a silica gel column, washing with 7:1 petroleum ether/chloroform, collecting the target product and vacuum drying to obtain the curcumin alkyl esters as final product.

The objective of the invention and technical problem to be solved in the invention can also be achieved by way of the technical measures shown as follows.

The method for the preparation of the long acting curcumin derivative as recited above, wherein the reaction in the ice water bath is monitored by thin layer chromatography (TLC) which is developed with 3:1 chloroform/ethyl acetate.

The method for the preparation of the long acting curcumin derivative as recited above, wherein the fatty acylates, unsaturated fatty acylates or aromatic acylates are each independently selected from decanoyl chloride, linoleoyl chloride or salicyloyl chloride.

The method for the preparation of the long acting curcumin derivative as recited above, wherein the cuminoids are selected from curcumin, demethoxycurcumin or bisdemethoxycurcumin.

The invention also discloses use of said long acting curcumin derivatives for the preparation of anti-depression medicine.

Use for the preparation of anti-depression medicine as recited above, wherein said long acting curcumin derivative comprises a pharmaceutically acceptable carrier, such as excipient, additive and flavor, and is prepared into various formulations, including powder, tablet, pellet, capsule, micro-capsule, granule or liquid derivatives.

Use for the preparation of anti-depression medicine as recited above, wherein said long acting curcumin derivative is used for the preparation of anti-depression beverage, food, food additives or health care products.

In addition, the invention further discloses use of said long acting curcumin derivatives for the preparation of anti-tumor medicine.

Use for the preparation of anti-tumor medicine as recited above, wherein said long acting curcumin derivative comprises a pharmaceutically acceptable carrier, such as excipient, additive and flavor, and is prepared into various formulations, including powder, tablet, pellet, capsule, micro-capsule, granule or liquid derivatives.

Use for the preparation of anti-tumor medicine as recited above, wherein said long acting curcumin derivative is used for the preparation of antitumor beverage, food, food additives or health care products.

Use for the preparation of anti-tumor medicine as recited above, wherein the tumor includes leukaemia, cervical cancer, renal cancer, breast cancer, gastric cancer, colonic cancer, lung cancer cells, liver cancer, prostate cancer, esophageal cancer, myeloma, glioma, melanoma, lymphoma, bladder cancer, adenocarcinoma, ovarian cancer, or skin cancer.

By means of above technical solutions, the inventive long acting curcumin derivatives, preparation method and pharmaceutical use thereof have at least the following advantages:
1) prolonged drug effect;
2) increased ester-solubility; improved bioavailability;
3) safe and non-toxicity.

The above description is merely a brief summary of the inventive technical solutions. In order to understand the inventive technical solutions more clearly, to practice in accordance with the invention, to enable the above and other objectives, characteristics and advantages to be more obvious and easier to be understood, the following specifically preferable embodiments are provided and illustrated with the figures shown as follows.

BEST MODES FOR CARRYING OUT THE INVENTION

In order to further set forth the technical means for achieving the expected objectives of the invention and efficacy thereof, the specified embodiments, methods, steps, characteristics and efficacy of the inventive long acting curcumin derivatives, preparation method and pharmaceutical use thereof will be further illustrated by referring to Figures in connection with preferable Examples, shown as follows.

Example 1

The inventive long acting curcumin derivatives are esters generated from the esterification reaction between cuminoids and C1-C50 saturated fatty acids, shown as follows:

The curcumin alkyl ester generated as above was prepared by the method comprising the following steps.

First, 2~4 mmol cuminoids was weighed and dissolved into 50 mL dioxane. Following the addition of 0.3~0.73 g pyridine, 3.6~8.60 mmol decanoic acid was added to the system dropwise. The system was allowed to react for 1~2 hours in an ice water bath. The reaction was monitored by TLC, which was developed with 3:1 chloroform/ethyl acetate.

The product obtained as above was poured into 40 mL petroleum ether for filtering. The resultant precipitate was dissolved into 30 mL ethyl acetate. The solution was washed twice with 20 mL of 1 mol/L hydrochloric acid solution and once with saturated sodium carbonate solution. The resultant material was dried for 2 h by adding 3 g anhydrous sodium sulfate. Subsequently filtration was performed and the filtrate was removed by spinning. Then the crude product curcumin decanoate was obtained.

The above crude product curcumin decanoate was loaded onto a silica gel column and diluted with 7:1 petroleum ether/chloroform. The target product was collected and dried in vacuum to obtain 1.07~1.67 g final product, i.e. curcumin decanoate.

In this Example, the cuminoids can also be selected from demethoxycurcumin or bisdemethoxycurcumin, wherein the added raw material decanoic acid is merely one of C1-C50 saturated fatty acids, which is intended to be illustrative but not restrictive. Other saturated fatty acids were prepared as above, only except that the addition amount of raw material may be different.

Figure 1:
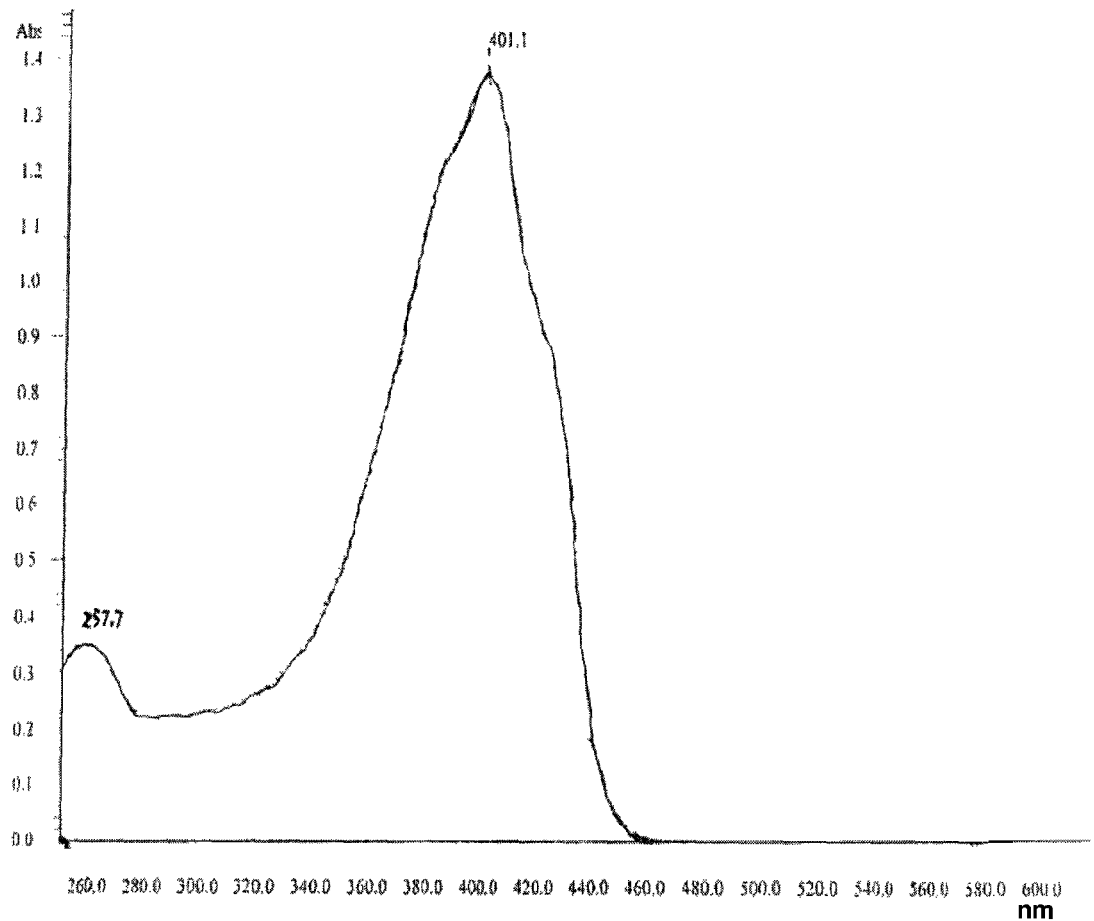
FIG. 1 is the ultraviolet absorption spectrum of the invention.
Figure 2:
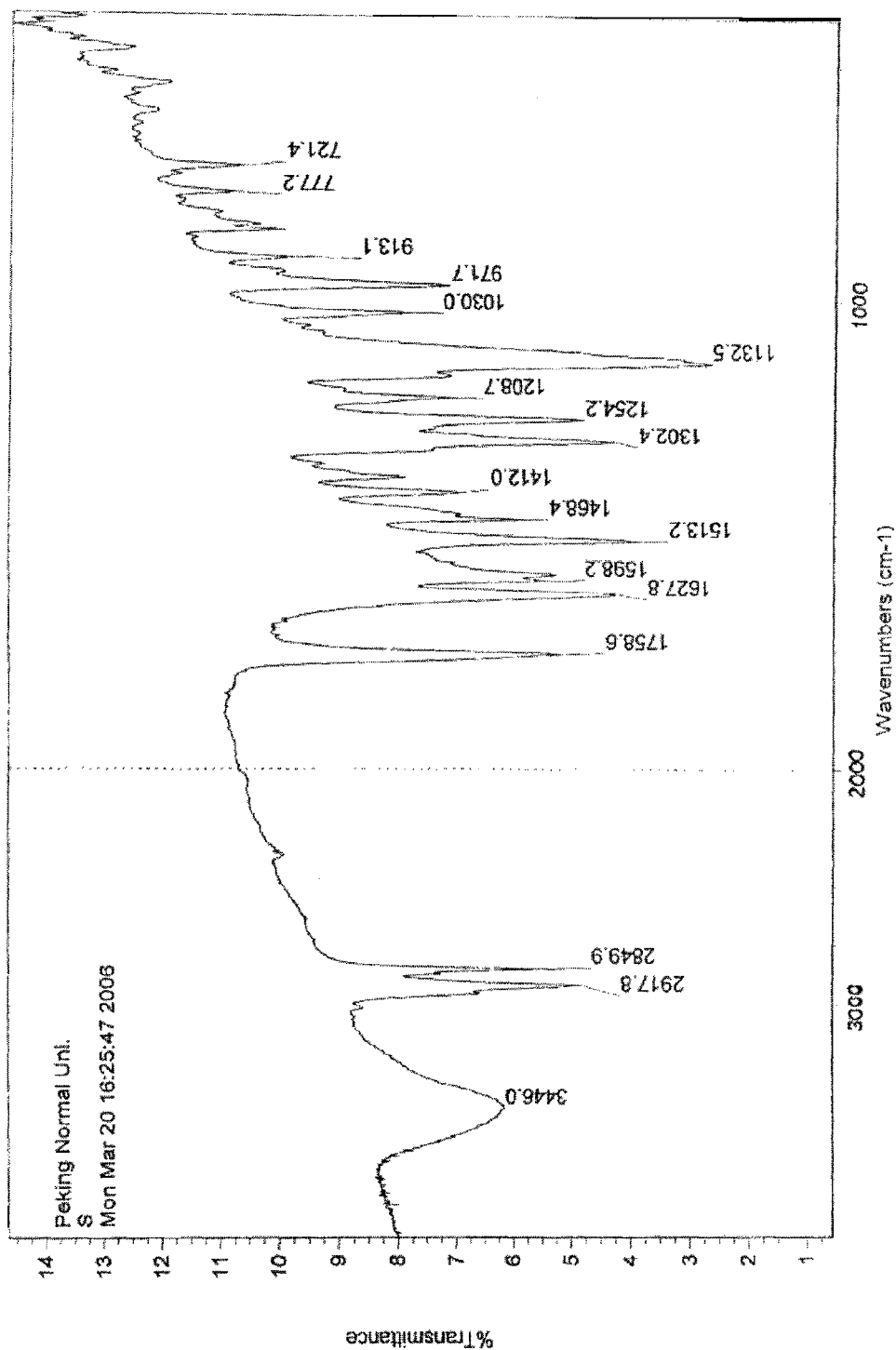
FIG. 2 is the infrared absorption spectrum of the invention.
Figure 3:
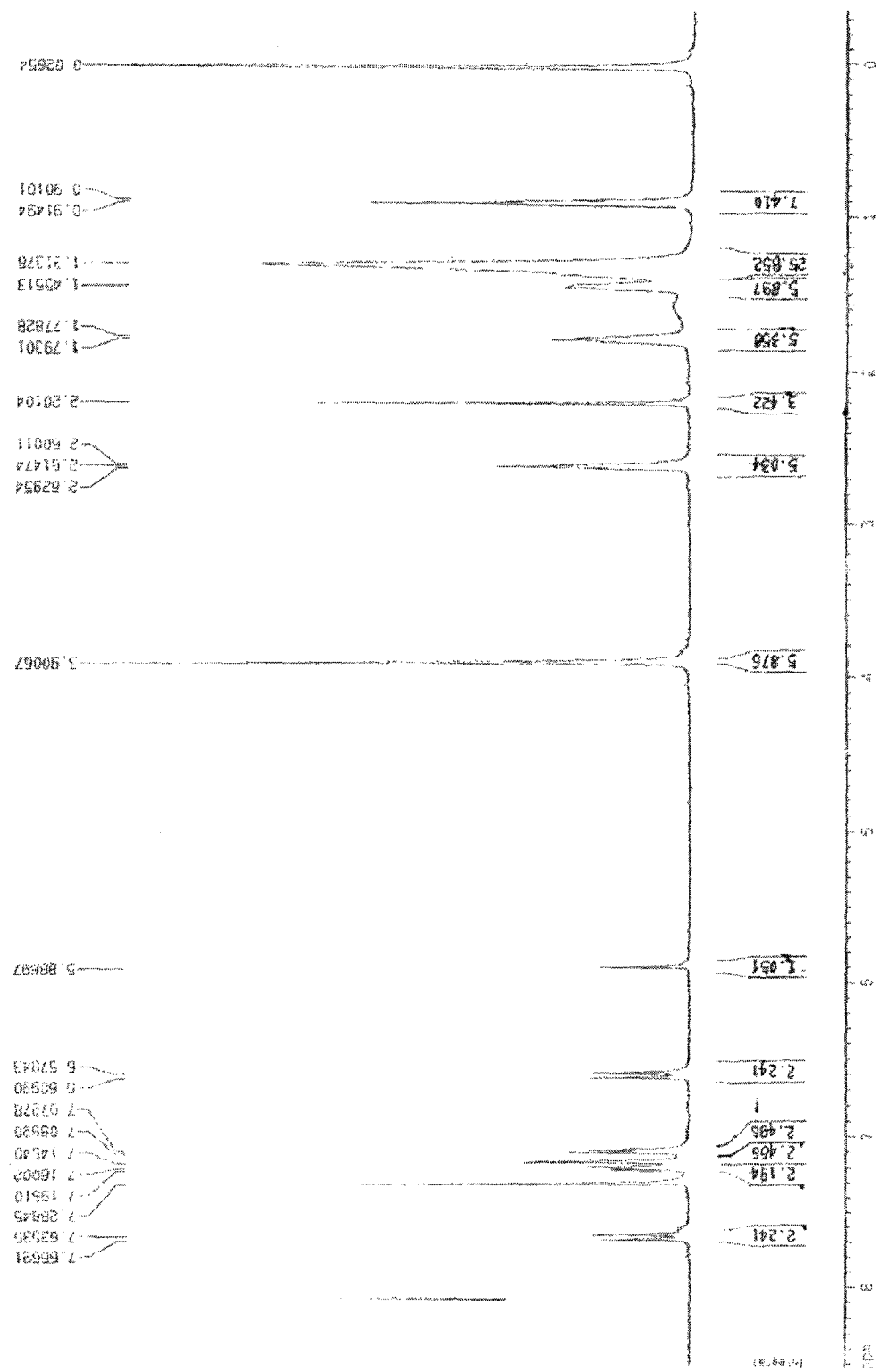
FIG. 3 is the nuclear magnetic resonance spectrum of the invention.

As shown in FIGS. 1~3, the curcumin decanoate prepared by this Example was confirmed to possess an expected structure of curcumin decanoate by using an ultraviolet absorption detection, an infrared absorption detection or a nuclear magnetic resonance detection.

Example 2

The inventive long acting curcumin derivatives are esters generated from the esterification reaction between cuminoids and C1-C50 saturated fatty acylates, shown as follow:

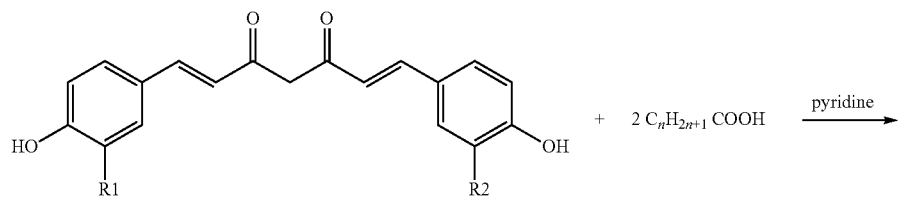

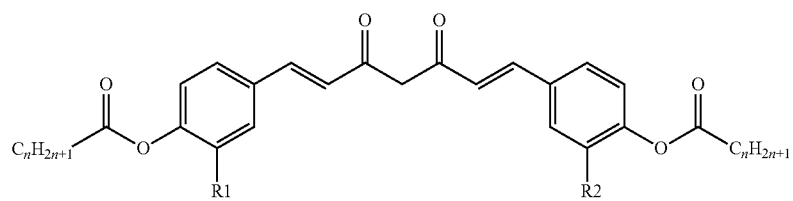

wherein, n=1~49.

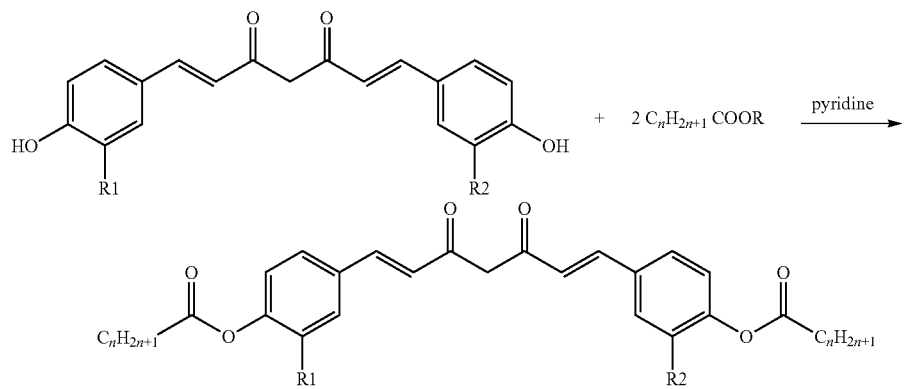

wherein, n=1~49, and in $C_nH_{2n+1}COOR$, R is halogen atom such as Cl, Br, or I, etc.

The curcumin alkyl ester generated as above was prepared by the method comprising the following steps.

First, 2~4 mmol cuminoids was weighed and dissolved into 50 mL dioxane. Following the addition of 0.3~0.73 g pyridine, 3.6~8.60 mmol decanoyl chloride was added to the system dropwise. The system was allowed to react for 1~2 hours in an ice water bath. The reaction was monitored by TLC, which was developed with 3:1 chloroform/ethyl acetate.

The product obtained as above was poured into 40 mL petroleum ether for filtering. The resultant precipitate was dissolved into 30 mL ethyl acetate. The solution was washed twice with 20 mL of 1 mol/L hydrochloric acid solution and once with saturated sodium carbonate solution. The resultant material was dried for 2 h by adding 3 g anhydrous sodium sulfate. Subsequently filtration was performed and the filtrate was removed by spinning. Then the crude product curcumin decanoate was obtained.

The above crude product curcumin decanoate was loaded onto a silica gel column and diluted with 7:1 petroleum ether/chloroform. The target product was collected and dried in vacuum to obtain 1.07~1.67 g final product, i.e. curcumin decanoate.

In this Example, the cuminoids can also be selected from demethoxycurcumin or bisdemethoxycurcumin, wherein the added raw material decanoyl chloride is merely one of C1-C50 saturated fatty acylates, which is intended to be illustrative but not restrictive. Other saturated fatty acids were prepared as above, only except that the addition amount of raw material may be different.

As shown in FIGS. 1~3, by using an ultraviolet absorption detection, an infrared absorption or a nuclear magnetic resonance detection, the curcumin decanoate prepared by this Example was confirmed to be the desired curcumin decanoate with the structural formula shown as follow.

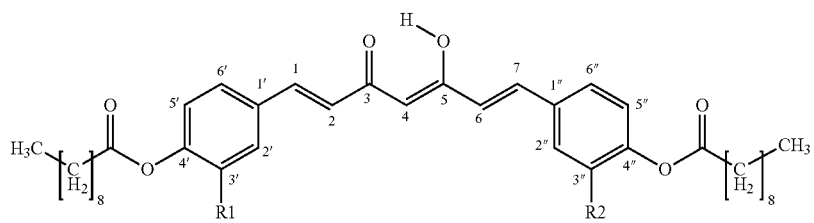

Example 3

The inventive long acting curcumin derivatives are esters generated from the esterification reaction between cuminoids and C1-C50 unsaturated fatty acids or the acylates thereof, shown as follow:

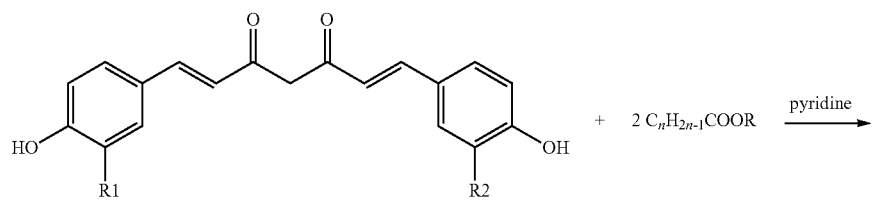

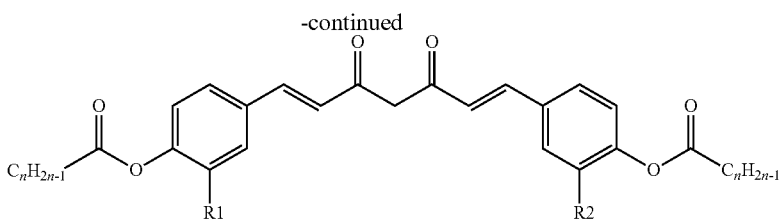

wherein, n=1~49, and in $C_nH_{2n-1}COOR$, R is halogen atom such as Cl, Br, or I, etc.

The curcumin alkenyl ester generated as above was prepared by the method comprising the following steps.

First, 2~4 mmol cuminoids, 140 mL dichloromethane and 73.4 mL pyridine were weighed. Then 100 mL of 0.229 mol linoleoyl chloride in dichloromethane was added dropwise over 1 h with agitation at room temperature, and allowed to react for 3 hours at a constant temperature of 50° C. The reaction was monitored by TLC which was developed with 3:1 chloroform/ethyl acetate. After the end point had been reached, the reaction mixture was transferred into a mixture of 200 mL water and 200 mL dichloromethane. The organic phase was washed twice with 20 mL of 1 mol/L hydrochloric acid solution and then once with saturated sodium carbonate. The resultant material was dried out by adding 3 g anhydrous sodium sulfate. Subsequently a filtration was performed and the filtrate was removed by spinning. Then the crude product curcumin linoleate was obtained.

The above crude product curcumin linoleate was loaded onto a silica gel column and diluted with 7:1 petroleum ether/chloroform. The target product was collected and dried in vacuum to obtain 1.07~1.67 g final product, i.e. curcumin decanoate.

In this Example, the cuminoids can also be selected from demethoxycurcumin or bisdemethoxycurcumin, wherein the added raw material linoleoyl chloride can also be palmitoleic acid, oleic acid, linolenic acid, arachidonic acid, DHA or eicosapentaenoic acid (EPA), which are necessary for human body. Other unsaturated fatty acids were prepared as above, with the only exception that an different amount of raw material was added.

In this Example, the raw material linoleoyl chloride may also be selected from other linear or branched unsaturated fatty acids and the unsaturated fatty acids with one or more double bonds at different positions and in different orders. The structure of curcumin derivatives, shown as follow, was confirmed by an element analysis, IR or FAB-MS.

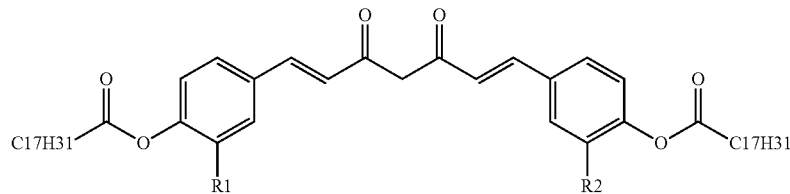

Example 4

The inventive long acting curcumin derivatives are esters generated from the esterification reaction between cuminoids and C1-C50 aromatic fatty acids or the acylates thereof, shown as follow:

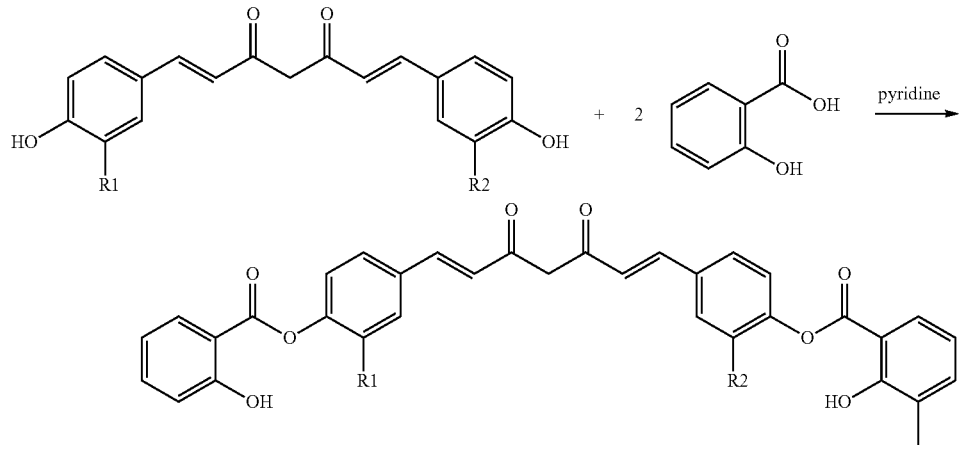

The curcumin aryl ester generated as above was prepared by the method comprising the following steps.

First, 2~4 mmol cuminoids was weighed and dissolved into 50 mL dioxane. Following the addition of 0.3~0.73 g pyridine, 3.6~8.60 mmol salicylic acid or salicyloyl chloride was added to the system. The system was allowed to react for 2 hours in an ice water bath. The reaction was monitored by TLC which was developed with 3:1 chloroform/ethyl acetate.

The product obtained as above was poured into 40 mL petroleum ether for filtering. The resultant precipitate was dissolved into 30 mL ethyl acetate. The solution was washed twice with 20 mL of 1 mol/L hydrochloric acid solution and once with saturated sodium carbonate solution. The resultant material was dried for 2 h by adding 3 g anhydrous sodium sulfate. Subsequently filtration was performed and the filtrate was removed by spinning. Then the crude product curcumin salicylate was obtained.

The above crude product curcumin salicylate was loaded onto a silica gel column and diluted with 7:1 of petroleum ether to chloroform. The target product was collected and dried in vacuum to obtain 1.07~1.67 g final product, i.e. curcumin salicylate.

In this Example, the cuminoids can also be selected from demethoxycurcumin or bisdemethoxycurcumin, wherein the added raw material salicylic acid or salicyloyl chloride may also be selected from other aromatic fatty acids or the acylates thereof. Other aromatic fatty acids or the acylates thereof were prepared as above, with the only exception that a different amount of raw material was added.

The curcumin salicylate prepared by this Example was confirmed to possess the correct structure, by using an ultraviolet absorption detection, an infrared absorption detection or a nuclear magnetic resonance detection.

Based on above Examples 1~6, it is known that the inventive curcumin derivatives are generated from the esterification reaction between cuminoids and C1-C50 saturated fatty acids or the acylates thereof, C1-C50 unsaturated fatty acids or the acylates thereof, and C1-C50 aromatic fatty acids or the acylates thereof. Esterified curcumin enters into human body and is decomposed into two parts, i.e. an ester and curcumin, wherein the ester enters into metabolism of the oxidative pathway and curcumin can exert a drug effect. In addition, esterified curcumin has a higher ester-solubility than curcumin itself, and the drug effect can be maintained accordingly. Just like the cuminoids in the prior art, the inventive curcumin derivative has a very broad application in the medical field. For example, it can be used for treating depression, cancer, hepatic fibrosis, or chronical renal failure, etc. The inventive curcumin derivatives also has a better slow-release effect than curcumin. The medical use and pharmaceutical effect of the inventive curcumin derivative were confirmed by using the following animal experiments.

In order to further investigate the long acting feature and the anti-depression effect of the curcumin derivatives prepared by the above method according to the invention, the inventors carried out a variety of animal experiments, including detection of curcumin in plasma of mice, an acute anti-depression experiment of mice, a chronic stress anti-depression experiment of rats, a sugar preference experiment of rats, and serological detection. The experimental results confirmed that the curcumin derivatives maintained the original drug effect of curcumin, overcame the defect of short action period of curcumin, prolonged drug effect, and thus achieved the expected functions. Protocols and results of the experiments are shown as follows.

Experimental Example 1

Detection of Curcumin in Plasma of Mice

Administration Pathway: Mice were administered by subcutaneous injection, with a dosage of 100 mg/kg body weight. Blood samples were collected from eye at 5 min, 10 min, 30 min, 45 min, 1 h, 1.5 h, 2 h, 6 h and Day 2, 3, 4, 5, 6, 7 after administration, respectively, with 6 mice/sampling point. The blood samples were placed into blood collection tubes which had been coated with heparin, and then centrifuged. Subsequently, 0.2 ml supernatant was collected, extracted twice with ethyl acetate, frozen and dried out in vacuum, dissolved in methanol to make a final volume of 0.2 ml, and used for HPLC assay.

Determination of the Standard Curve

Approximately 0.5 mg curcumin was added to a certain amount of peanut oil, to resulting in a final concentration of 0.5 mg/ml. Different concentrations of curcumin was added to a blank plasma sample precisely. The standard samples were prepared in accordance with the plasma samples.

HPLC-MS/MS Assay of Curcumin

Conditions of Spectrum:
 chromatographic column: Waters XTrra C18 reversed-phase column (2.1×150 mm, 5 μm);
 mobile phase: methyl cyanide/0.1% aqueous formic acid solution (97:3, v/v);
 velocity of flow: 300 μl/min;
 temperature of column: 40° C.
 loading amount: 20

Conditions of Mass Spectrum:
 ESI ion source, anion detection;
 Curtain Gas (CUR): 10 L/min;
 Collision Gas (CAD): medium;
 Ion Spray Voltage (1S): −4500 V;
 Temperature (TEM): 500° C.;
 Ion Source Gas 1 (GS1): 40 L/min; and
 Ion Sourse Gas 2 (GS2): 40 L/min.

Selective multi-reaction monitoring, ion reaction for quantitative analysis and the corresponding Declustering Potential (DP), Collision Energy (CE), Entrance Potential (EP) are m/z 367.1~216.9, DP: −50 V, CE: −15 V, EP: −6 V, respectively.

Figure 4:
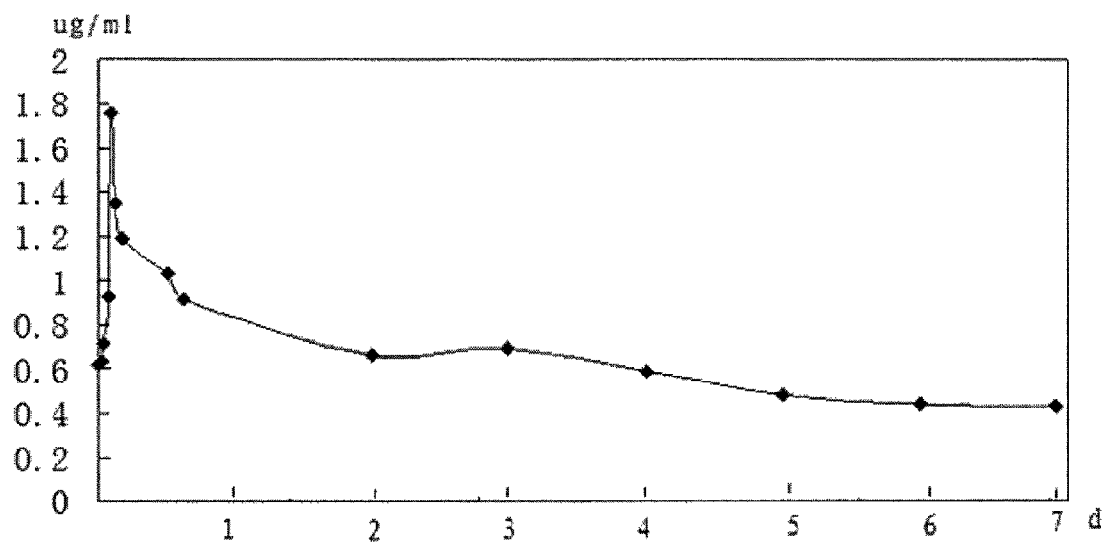
FIG. 4 is the curve diagram of curcumin detected in the mice of the invention.

As shown in FIG. 4, blood samples were collected by removing eye balls at 5 min, 10 min, 30 min, 45 min, 1 h, 1.5 h, 2 h, 6 h and Day 2, 3, 4, 5, 6, 7 after administration, respectively. The content of curcumin in the plasma was measured by HPLC-MS/MS. As shown in FIG. 4, after a single administration, the content value of curcumin in the plasma reached peak in Day 1, then entered into a plateau period until Day 7. By then, curcumin can still be detected in plasma of mice.

Experimental Example 2

The Acute Anti-Depression Experiment 2.1 The Tail Suspension Test in Mice

Figure 5:
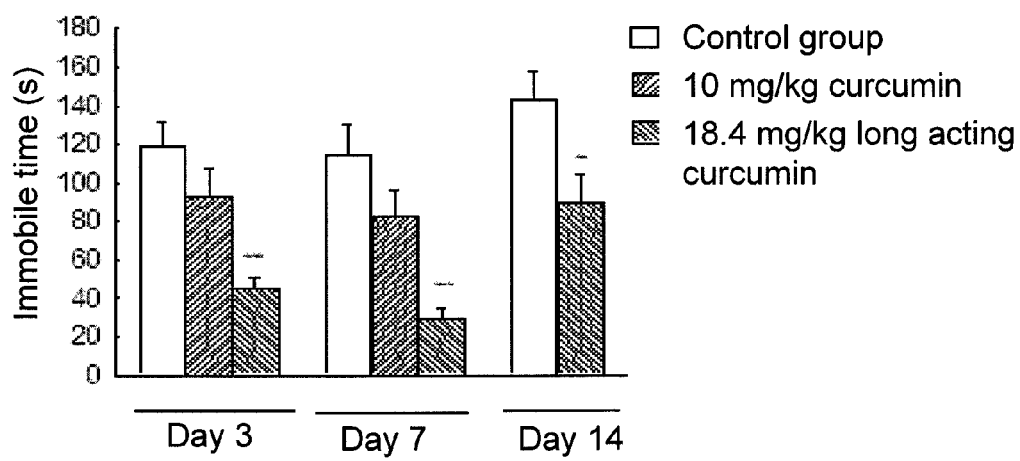
FIG. 5 is the diagram showing the results of the tail suspension test in the invention (n=15, mean±S.E.M).

Please see FIG. 5, three groups were classified (24 male ICR mice/group): a control group, a curcumin group (10 mg/kg), and a long acting curcumin group (18.4 mg/kg, a single administration of the dosage for 20 days). The tail suspension test was carried out for each of these groups on Days 3, 7 and 14 after administration, except that such experiment was not performed for the curcumin group on Day 14. Tails of the mice were taped on a special iron stand at 1 cm from the tips, whilst keeping the mice staying at a height of 50 cm from ground. Performance of the mice was observed within 6 min, and the accumulative immobile time within the last 4 min was recoded for each mouse.

It was indicated from the tail suspension test of mice that on Days 3 and 7 after administration, 10 mg/kg curcumin resulted in no significant difference in the reduction of tail suspension accumulative immobile time. Compared with the control group, 18.4 mg/kg long acting curcumin reduced the accumulative immobile time by 50.7% when measured 3 days after administration; and reduced the accumulative immobile time by 59.5% when measured 7 days after administration; and reduced the accumulative immobile time by 31.8% when measured 14 days after administration (*P<0.05,  P<0.01, and * P<0.001, compared with the control group).

2.2 Forced Swimming Test of Mice

Figure 6:
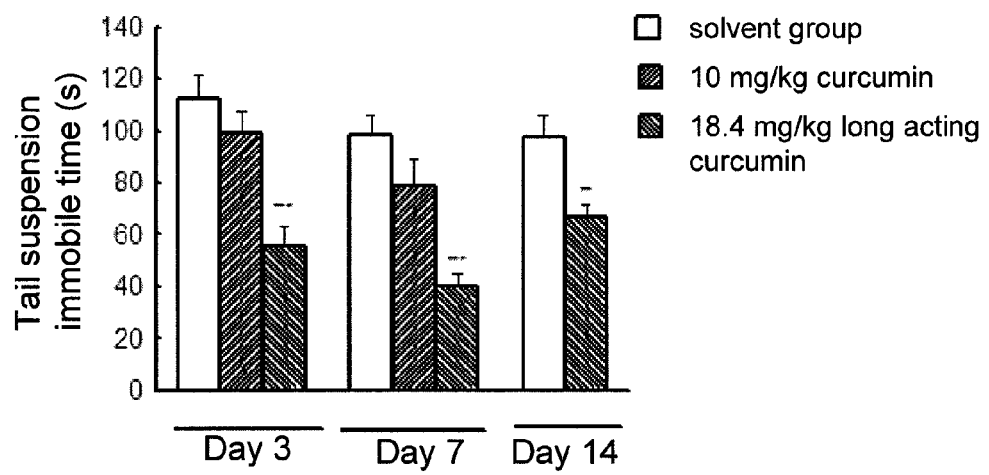
FIG. 6 is the diagram showing the influence of the invention on the immobile time of the mice in the forced swimming test (n=15, mean±S.E.M).

Please see FIG. 6, three groups were classified (24 male ICR mice/group): a control group, a curcumin group (10 mg/kg), and a long acting curcumin group (18.4 mg/kg, a single administration of the dosage for 20 days). The mice were forced to swim on Days 3, 7 and 14 after administration, except that such experiment was not performed for the curcumin group on Day 14.

Twenty four hours before the formal test, the mice were placed into a round glass container (height: 25 cm, diameter: 10 cm) filled with water (depth: 10 cm) with a temperature of 24±1° C., and forced to conduct swim training for 15 min. Twenty four hours later, the mice were placed into the round glass container filled with water (depth: 10 cm) again and forced to swim for 6 min. The accumulative immobile time within the last 4 min was observed and recorded for each mouse. The immobile time is intended to mean the period within which the mouse stops to struggle, floats in the water and keeps immobile, or only makes a few slight movements that are necessary to keep its head floating on the surface of water.

The results of the forced swimming test of mice on Days 3 and 7 after administration showed that 10 mg/kg curcumin did not significantly reduce the accumulative immobile time in the forced swimming test. Compared with the control group, 18.4 mg/kg long acting curcumin reduced the accumulative immobile time by 62.1% when measured 3 days after administration; reduced the accumulative immobile time by 74.7% when measured 7 days after administration; and reduced the accumulative immobile time by 37.8% when measured 14 days after administration (*P<0.05,  P<0.01, and * P<0.001).

2.3 Detection of Monoamine and Metabolites Thereof in Brains of Mice

On Days 3 and 7 after administration (long acting curcumin), mice were sacrificed by rapid decollation. Hippocampus was collected immediately on ice, weighed, put into an Eppendorf tube and kept in refrigeratory at −80° C.

To each 100 mg brain tissue, 200 µl ice-cooled Solution A (0.4 mol/L $HCLO_4$) was added. The mixture was homogenized ultrasonically in a ice bath, kept in dark at 4° C. for 60 min, and centrifuged for 20 min (12,000 rpm, 4° C.). The supernatant was collected and added with a half volume of Solution B (0.2 mol/L potassium citrate, 0.3 mol/L $K_2HPO_4$ and 0.2 mol/L EDTA). The mixture was vortexed thoroughly for 10 min, kept at 4° C. in dark for 60 min, and centrifuged again for 20 min (12,000 rpm, 4° C.). The supernatant was collected and measured for the content of monoamine.

The contents of 5-HT, NA, DA, 5-HIAA and DOPAC in brain tissue were determined by High Effective Liquid Phase Electrochemistry. The filtered (aperture: 0.22 µm) supernatant (20 µl) of the sample was loaded automatically onto the chromatographic column Diamonsilim C18 (150×4.6 mm ID., 5 µm), at a flow velocity of 1.0 ml/min. The mobile phase was composed of 125 mmol/L citric acid-sodium citrate buffer (pH=4.3), 0.1 mmol/L EDTA, 1.2 mmol/L octyl sodium sulfonate, and 16% methanol. Working voltage of the detector was 50, 100, 200, 300, 400 and 500 mV. The contents of monoamine and metabolites thereof in brain tissue were shown as ng/g wet tissue weight.

As shown in Table 1, long acting curcumin (18.4 mg/kg) raised the content of 5-HT in hippocampus and also the level of noradrenalinon on Days 3 and 7. The conversion rate of 5-HT in hippocampus showed a downtrend in the long acting curcumin group.

TABLE 1

The influence of long acting curcumin on 5-HT, NA, DA and metabolites thereof in hippocampus regions of mice (n = 12, mean ± S.E.M)

| Group | Dosage (mg/kg) | 5-HT | 5-HIAA | 5-HIAA/5-HT | Noradrenaline | Dopamine | DOPAC |
|---|---|---|---|---|---|---|---|
| Control |  | 532.4 ± 23.6 | 177.9 ± 14.9 | 0.34 ± 0.03 | 245.2 ± 19.5 | 18.6 ± 4.6 | 12.3 ± 2.2 |
|  |  | 534.0 ± 26.0 | 177.1 ± 14.0 | 0.32 ± 0.02 | 241.5 ± 28.4 | 18.9 ± 1.7 | 12.9 ± 2.7 |
| Curcumin | 10 | 541.2 ± 31.8 | 175.7 ± 13.8 | 0.32 ± 0.03 | 245.6 ± 12.2 | 19.1 ± 3.6 | 12.4 ± 1.2 |
|  | 10 | 534.6 ± 28.9 | 179.2 ± 14.9 | 0.33 ± 0.03 | 246.6 ± 11.2 | 18.8 ± 5.4 | 11.9 ± 1.8 |
| Long acting curcumin | 18.4 | 713.1 ± 19.2** | 183.4 ± 14.2 | 0.25 ± 0.02 | 369.9 ± 12.3** | 20.3 ± 5.9 | 13.1 ± 2.0 |
|  | 18.4 | 725.0 ± 30.4** | 186.3 ± 8.4 | 0.25 ± 0.03 | 372.2 ± 21.6** | 21.2 ± 5.6 | 14.6 ± 2.1 |

*P < 0.05,
**P < 0.01, compared with Control.

Experimental Example 3

Chronic Stress Anti-Depression Experiment of Rats 3.1 Establishment of a Mouse Chronic Stress Model Animals were divided into 6 groups (12 male SD rats per group), including a normal control group, a model group, a low dosage group (4.6 mg/kg), a medium dosage group (9.2 mg/kg), a high dosage group (18.4 mg/kg) and a positive control group (imipramine). The administration group and model group were administered once every 7 days, and the dosage for each administration was the total dosage for 7 days; whereas imipramine was given daily. Different dosages of long acting curcumin (4.6, 9.2 and 18.4 mg/kg, total dosages for 7 days) were subcutaneously administrated in one time. Imipramine (10 mg/kg) was injected intraperitoneally for 21 days. The experiment started at 30 min after the final administration (imipramine). The rats in the normal control group were raised normally under a condition without any stimulation except for weighing body weight, measuring body temperature, and subjected to sugar test. All of other groups were subjected to stimulations of same type and same strength. During the experiment, different types of stimulations were applied in an unpredictable manner, and the same type of stimulation was enhanced each time.

The chronic stress course was 20 days in total, once per day, from 9:00 AM to 2:00 PM. The stress protocol was shown as follows: horizontally shaking at a high speed for 45 min; nipping tails (1 cm from the tail root): 1 min; depriving of water for 24 h; forbidding moving for 1.5 h; fasting for 24 h; stimulating with ice water (water temperature: 10° C.) for 5 min; electric shocking (1 mA, time course: is, 1 shock/min) the bottoms of feet for 30 min; changing cages and raising separately for 24 h; forbidding moving for 2 h; nipping tails (1 cm from the root of tail) for 1 min; depriving of water for 24 h; horizontally shaking at a high speed for 1.5 h; fasting for 24 h; nipping tails (1 cm from the tail root): 1 min; electric shocking (1 mA, time course: 1 s, 1 shock/min) the bottoms of feet for 40 min; stimulating with ice water for 5 min; changing cages and raising separately for 24 h; horizontally shaking at a high speed for 60 min; electric shocking (1 mA, time course: 1 s, 1 shock/min) the bottoms of feet for 50 min; depriving of water for 24 h; forbidding moving for 2.5 h; and 24 h social isolation.

3.2 Measurement of Body Temperature of Rats

The front part of a digital thermometer was coated with liquid paraffin, and then inserted into the anus of a rat with a depth of approximately 1 cm. The temperature was read twice accordingly and averaged.

After the chronic stress for 21 days, the body temperature of the rats in the model group was lower evidently and showed a significant difference, compared with the normal rats. The body temperatures of all of the rats administered with various dosages of long acting curcumin were increased to some extent, compared with the stress control group. Imipramine had no obvious impact on the body temperatures of the stressed rats, as shown in Table 2.

TABLE 2

The influence of long acting curcumin on the body temperature of chronically stressed rats (° C.) (n = 10~12, mean ± S.E.M.).

| Group | Dosage (mg/kg) | Body temperature before stress | Body temperature after stress |
|---|---|---|---|
| Control group | | 36.99 ± 0.136 | 37.05 ± 0.068 |
| Model group | | 36.93 ± 0.140 | 36.46 ± 0.122### |
| Long acting curcumin group | 4.6 | 37.06 ± 0.125 | 37.40 ± 0.079*** |
| | 9.2 | 37.06 ± 0.158 | 37.45 ± 0.074*** |
| | 18.4 | 37.00 ± 0.122 | 37.48 ± 0.088*** |
| Imipramine group | 10 | 36.83 ± 0.142 | 36.34 ± 0.083 |

$P < 0.05$, ###$P < 0.001$ *$P < 0.05$, compared with Control group.
$P < 0.01$ and *$P < 0.001$, compared with Model group.

3.3 Sugar Water Test of Rats

Before this experiment, animals were trained to adapt to drink sugar water in a to quite room. Two bottles were placed simultaneously into each cage. For the first 24 h, these two bottles were both filled with 1% sugar water; and for the next 24 h, one of them was filled with 1% sugar water and the other was filled with pure water. Then after 23-hour water deprivation, the animals were tested for basic sugar water/pure water consumption. One bottle of 1% sugar water and one bottle of pure water were provided to each rat simultaneously. One hour later, the two bottles were weighed, and the total liquid consumption, sugar water consumption, pure water consumption, and the sugar water preference=sugar water consumption/total liquid consumption×100% were calculated, respectively. The experiment was performed after continuous administration of curcumin for 14 days.

Based on the sugar water test performed before the beginning of stress, it was found that there was no significant difference in the sugar water preference among all groups. However, from the sugar water test performed after the end of stress, it was shown that there existed an extremely significant difference in the sugar water preference between the normal control group and the model group. In other words, the sugar water preference of the rats in the model group was reduced significantly, compared with the normal control group. In the medium dosage group and the high dosage group, long acting curcumin did not improve the sugar water preference markedly, which was significantly different from the model control group. Long acting curcumin in the low dosage group, and imipramine did not influence the sugar water preference of the stressed rats, as shown in Table 3.

TABLE 3

The result of the sugar water test (%) (n = 10~12, mean ± S.E.M.).

| Group | Dosage (mg/kg) | Sugar water volume before stress (ml) | Sugar water volume after stress (ml) |
|---|---|---|---|
| Control group | | 73.3 ± 8.6 | 82.9 ± 4.3 |
| Model group | | 73.3 ± 8.3 | 59.4 ± 4.8### |
| Long acting curcumin group | 4.6 | 60.2 ± 9.2 | 54.1 ± 4.7 |
| | 9.2 | 60.4 ± 9.2 | 72.8 ± 3.1* |
| | 18.4 | 66.8 ± 8.6 | 71.6 ± 2.3* |
| Imipramine group | 10 | 74.8 ± 7.8 | 67.5 ± 5.0 |

$P < 0.05$, ###$P < 0.001$, compared with Control group.
*$P < 0.05$, $P < 0.01$ and *$P < 0.001$, compared with Model group.

3.4 Forced Swimming Test of Rats

Figure 7:
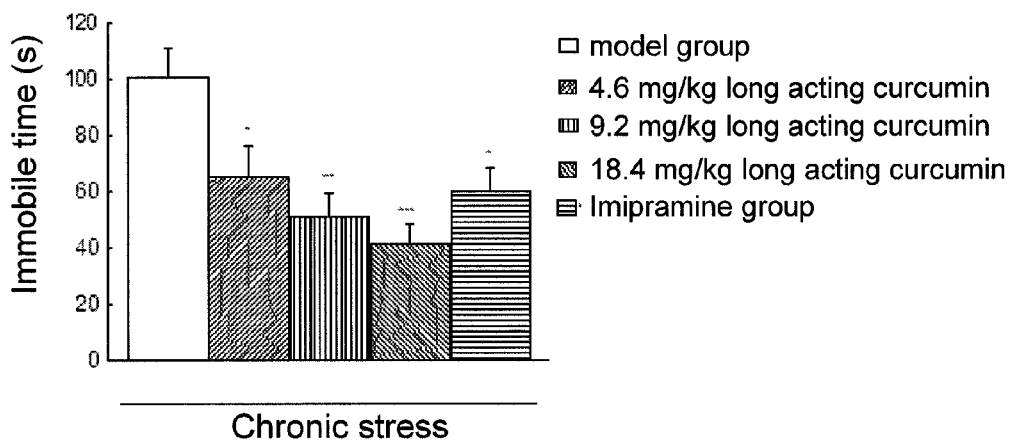
FIG. 7 is the diagram showing the influence of the invention on the immobile time of the rats in the forced swimming test (n=15, mean±S.E.M).

Please see FIG. 7. 24 hours before the formal test, rats were placed into a round glass container (height: 40 cm, diameter: 18 cm) filled with water (depth: 23 cm) with a temperature of 24±1° C., and forced to conduct swim training for 15 min. Thirty minutes after the final administration (imipramine), the rats were placed into the round glass container filled with water (depth: 23 cm) again and forced to swim for 6 min. The accumulative immobile time within the last 4 min was observed and recorded for each rat. The immobile time is intended to mean the period within which the rat stops to struggle, floats in the water and keeps immobile, or only makes a few slight movements that are necessary to keep its head floating on the surface of water.

The result of the forced swimming test of rats showed that 4.6, 9.2 and 18.4 mg/kg long acting curcumin reduced the accumulative immobile time of the forced swimming test by 37.6%, 49.4% and 58.9%, respectively, in a dose-dependent manner, compared with the model control group. The antidepression effect of the long acting curcumin in the forced swim model was similar to that of imipramine (10 mg/kg), a classic anti-depressive. Imipramine, in the forced swimming test, reduced the accumulative immobile time by 40.5%. *$P<0.05$,  $P<0.01$ and * $P<0.001$, compared with the control group.

3.5 Determination of the Content of Serum Corticosterone

In this experiment, the content of serum corticosterone was measured by a competitive method, with its mechanism shown as follow: antigens in samples and enzyme-labeled antigens compete to bind antibodies in a solid phase. The more antigens exist in samples, the less enzyme-labeled antigens bind to the solid phase, thereby resulting in a fainter coloration.

On the next day after the end of the 21-day stress period, rats were sacrificed by decollation, and 5~10 ml whole blood was collected. A portion of the collected whole blood was kept at room temperature for 20 min, followed by centrifugation at 1000 rpm for 10 min. Serum was then separated and stored at −80° C. The serum corticosterone detection kit was used for such detection.

The content of serum corticosterone of the rats in the model control group was significantly higher than that of the rats in the normal control group. As shown in Table 4, the content of corticosterone was remarkably decreased in the long acting curcumin groups and the imipramine group, compared with the model control group.

TABLE 4

The effect of long acting curcumin on serum corticosterone
(n = 6, mean ± S.E.M.).

| Groups | Dosage (mg/kg) | serum corticosterone (nmol/L) |
|---|---|---|
| Control group | | 219.4 ± 12.4 |
| Model group | | 314.8 ± 25.0[#] |
| Long acting curcumin group | 4.6 | 239.5 ± 33.7* |
| | 9.2 | 222.9 ± 30.6* |
| | 18.4 | 199.6 ± 28.0** |
| Imipramine group | 10 | 137.0 ± 15.3*** |

[#]$P < 0.05$, [###]$P < 0.001$, compared with Control group.
*$P < 0.05$, $P < 0.01$ and *$P < 0.001$, compared with Model group.

Results

By means of a single injection to a mouse, curcumin could be sustainedly detected in the mouse until Day 7, which indicated that such a medicine existed in the mouse continuously, and achieved an expected slow-release feature. The two desperation models were administered acutely. Compared with the model group, the accumulative immobile time did not changed remarkably in the curcumin group after 3 days and 7 days, but was reduced significantly in the long acting curcumin group after 3 days, 7 days and 14 days, respectively. The results for detecting monoamine transmitter of mice showed that the single administration increased the 5-HT content in the hippocampus regions of the mice in the long acting curcumin group on Days 3 and 7. Such results also indicated that anti-depression effect could still be maintained for at least one week after a single administration of the long acting curcumin derivative. In the chronic stress model of rat, chronic administration of long acting curcumin for 21 days (once every 7 days) could decrease the accumulative immobile time of swimming dramatically and reverse the downtrend of pleasant taste sensation in the sugar water preference experiment. The content of serum corticosterone was clearly increased in the stressed rats, whereas reduced significantly after the provision of long acting curcumin, which indicated that the long acting curcumin derivative has a continuous anti-depression effect in the stress model of rats.

It was known from the investigations of anti-depression effect in other animal models that long acting curcumin derivatives also maintained the intrinsic anti-depression effect of curcumin, whilst resulting in a slow release of drug and a prolonged drug effect. Therefore, long acting curcumin derivatives have a good prospect for clinic application.

Animal experiments showing the use of the inventive long acting curcumin derivatives in antitumor medicines and the results thereof will be introduced in Experimental Examples 4~9 shown below.

Experimental Example 4

Antitumor Experiment of Tumor S-180-Bearing Mice

Male ICR mice were divided into 5 groups (n=15/group), including long acting curcumin groups with high, medium and low dosages, respectively; and a positive control group administered with 5-FU. During the experiment, the mice were inoculated with S-180 sarcoma cells ($\times 10^7$) in armpits. The administration started on the next day, wherein the long acting curcumin group was provided with a 7-day dosage by a single administration, and the 5-FU group was administered daily. Seven days later, the mice were sacrificed by decollation. The tumors were removed, and the mice and the tumors were weighed separately.

Figure 8:
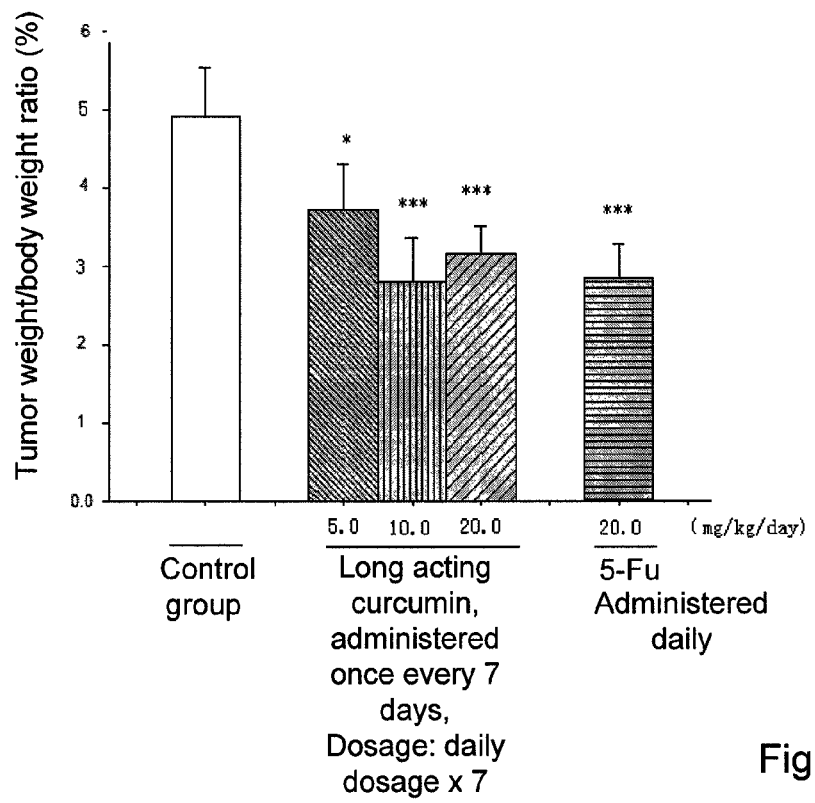
FIG. 8 is the experimental diagram showing the anti-tumor ability of the invention in the tumor S-180-bearing mice.

As shown in FIG. 8, there existed a significant difference in the tumor weight/body weight ratio between the long acting curcumin groups and the control group. The inhibitory rates of tumors were 28.5% in the low dosage group, 57.8% in the medium dosage group, 50.1% in the high dosage group, and 55.8% in the 5-FU group, respectively.

Experimental Example 5

Antitumor Experiment of Tumor HCT116-Bearing Mice

Male ICR mice were divided into 5 groups (n=15/group), including long acting curcumin groups with high, medium and low dosages, respectively; and a positive control group administered with 5-FU. During the experiment, the mice were inoculated with HCT116 cells ($\times 10^7$) in armpits. The administration started on the next day, wherein the long acting curcumin group was provided with a 7-day dosage by a single administration, and the 5-FU group was administered daily. Seven days later, the mice were sacrificed by decollation. The tumors were removed, and the mice and the tumors were weighed separately.

Figure 9:
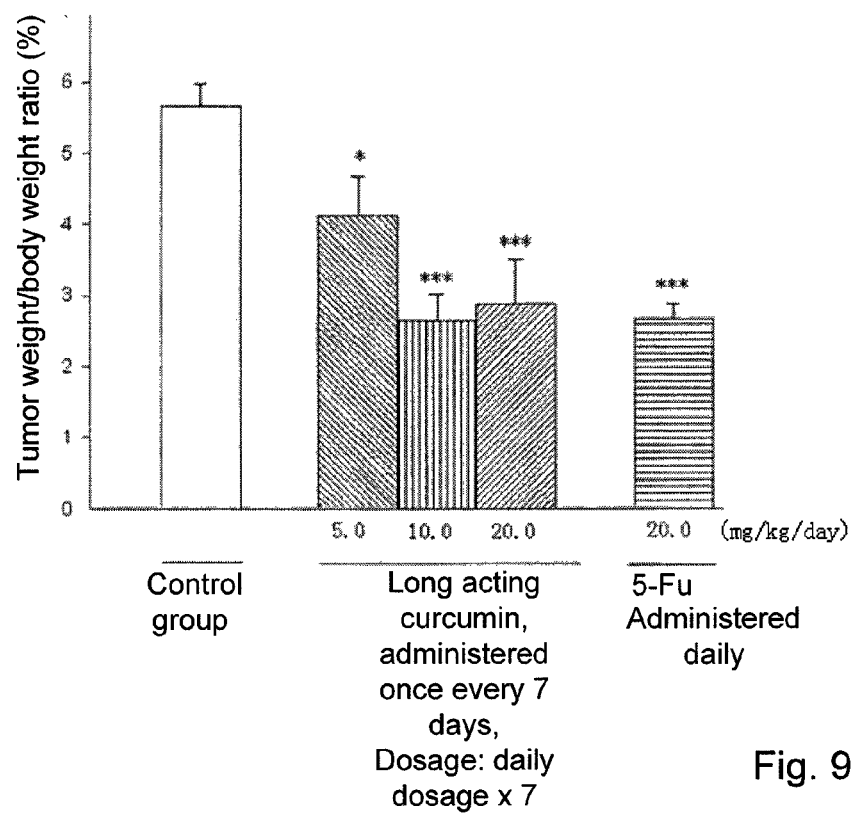
FIG. 9 is the experimental diagram showing the anti-tumor ability of the invention in the tumor HCT116-bearing mice.

As shown in FIG. 9, there existed a significant difference in the tumor weight/body weight ratio between the long acting curcumin groups and the control group. The inhibitory rates of tumors were 29.6% in the low dosage group, 58.4% in the medium dosage group, 49.3% in the high dosage group, and 52.8% in the 5-FU group, respectively.

Experimental Example 6

The Effect of Long Acting Curcumin on Apoptosis of Tumor Cells

Male ICR mice were divided into the following groups (n=15/group): a long acting curcumin group administered with 7-day dosage; a positive control group administered with 5-FU daily; and a control group administered with solvent. During the experiment, the mice were inoculated with S-180 cells ($\times 10^7$) in armpits. Seven days later, the mice were sacrificed by decollation and the tumors were removed. Tumor fluid was collected from tumors, and used for determining cell cycle by flow cytometry after ethanol fixation.

Figure 10:
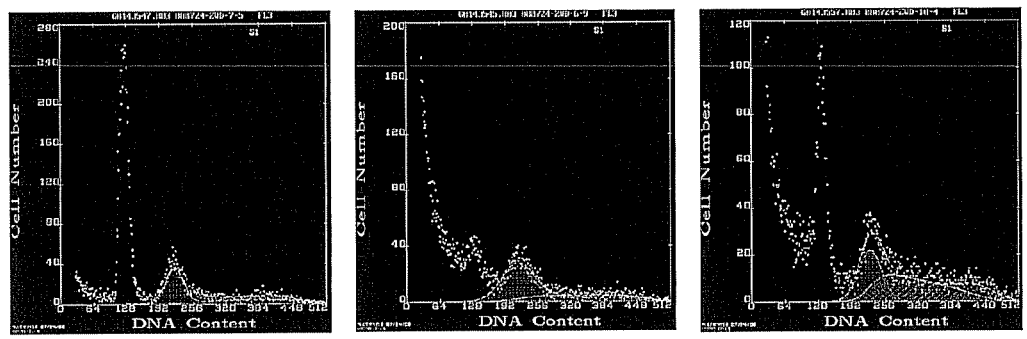
FIG. 10 is the experimental diagram showing the influence of the invention on apoptosis of tumor cells.

As shown in FIG. 10, apoptosis was promoted in the long acting curcumin group. The apoptosis level of tumor cells was 44.7 for the long acting curcumin group; 22.9 for the control group; and 29.1 for the 5-FU group, respectively (see Table 5 as well).

TABLE 5

The determination results of sarcoma cell cycle

| Groups | G1 | | | G2 | | | S | | APO |
|---|---|---|---|---|---|---|---|---|---|
| | MEAN | CV | % | MEAN | CV | % | % | G2/G1 | % |
| Control group | 220.9 | 9.4 | 56.9 | 465.2 | 3.3 | 0.9 | 42.2 | 2.106 | 22.9 |
| Administration group | 213.1 | 14.9 | 64.9 | 455.7 | 6.8 | 1.0 | 34.1 | 2.138 | 44.7 |
| 5-FU group | 226.3 | 9.7 | 35.1 | 433.1 | 8.0 | 11.7 | 53.2 | 1.914 | 29.1 |

Experimental Example 7

Survival Experiment of Tumor-Bearing Mice

Male ICR mice were divided into 2 groups (n=30/group): a long acting curcumin group provided with a 7-day dosage by a single administration; and a control group administered with a solvent. During the experiment, the mice were inoculated with S-180 sarcoma cells ($\times 10^5$) in armpits, and the next day the administration begins. The survival rate was recorded for each group.

Figure 11:
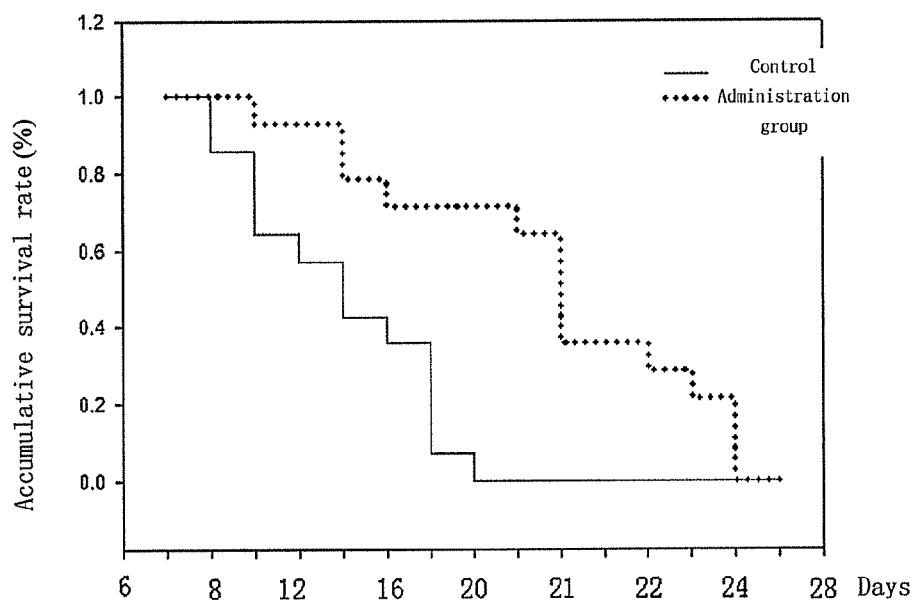
FIG. 11 is the experimental diagram showing the survival result of the tumor-bearing mice in the invention.

As shown in FIG. 11, the medium survival time was 13.5 days with a 95% confidence interval of 9.5~14.7 days in the control group, whereas the medium survival time was 17.5 days with a 95% confidence interval of 12.8~20.2 days in the long acting curcumin group. Kaplan-meier analysis showed that the difference of the survival time between these two groups was significant.

Experimental Example 8

Inhibitory Effect of Long Acting Curcumin on Tumor Cells

The tumor cells with a stable passage feature, including Hela tumor cells, renal cancer cells, breast cancer cells, gastric cancer cells, rectal cancer cells, pulmonary cancer cells, hepatic cancer cells HepG2, prostate cancer cells, esophageal cancer cells, sarcoma cells, glioma cells, melanoma cells, lymphoma cells, and bladder cancer cells, were counted under a microscope ($\times 10^4$), and cultured in a 96-well plate under $CO_2$ saturated water vapor for 24 h. To these cells, long acting curcumin (a final concentration of 25 μM) and the control solvent were added, respectively. After 72 h, the inhibitory effect of long acting curcumin on tumor cells was detected by MTT method, and the inhibitory rate was calculated.

Figure 12A:
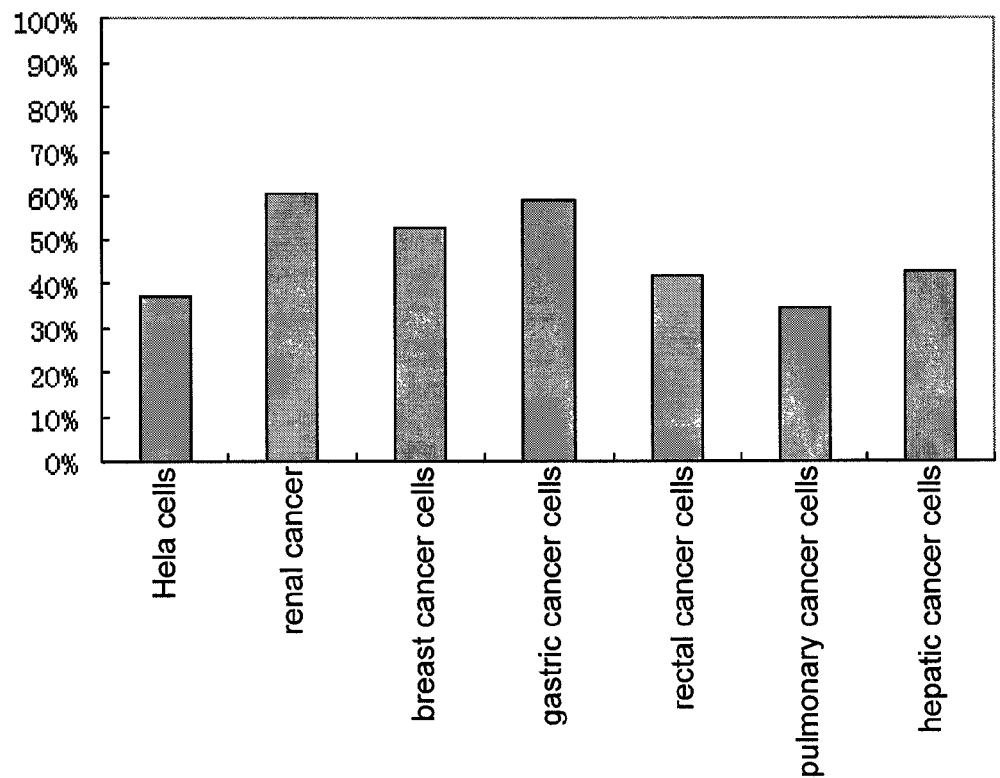
FIG. 12(a) and FIG. 12(b) are the experimental diagrams showing the inhibition effect of the invention on different tumor cells.
Figure 12B:
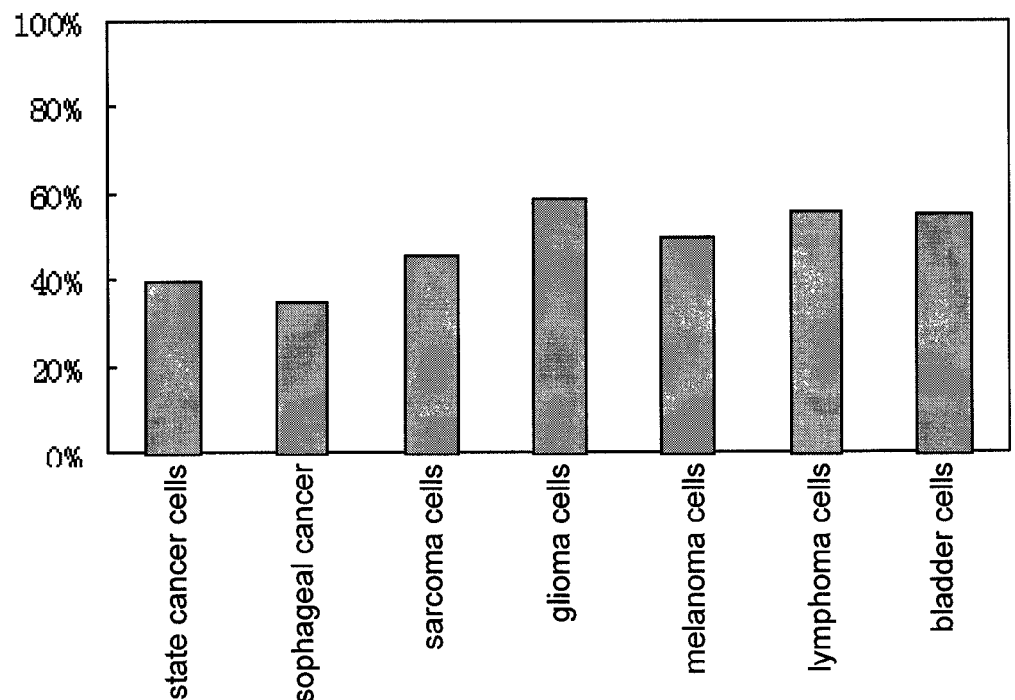

As shown in FIGS. 12(a) and 12(b), the inventive long acting curcumin derivatives inhibited all of these 14 types of cells (P<0.05) with different inhibitory rate for each cell type. The results were also shown in Table 6.

TABLE 6

The inhibitory effect of long acting curcumin on proliferation of tumor cells (P < 0.05)

| Type of cells | Inhibitory rate (%) |
|---|---|
| Hela cell | 37.3 ± 2.4 |
| Renal cancer cell 7860 | 60.6 ± 1.8 |
| Breast cancer cell BT474 | 52.7 ± 1.6 |
| Rectal cancer cell HCT116 | 58.9 ± 2.1 |
| Gastric cancer cell MGC80-3 | 42.6 ± 1.7 |
| Pulmonary cancer cell A549 | 35.9 ± 1.2 |
| Hepatic cancer cell HepG2 | 43.7 ± 1.4 |
| Prostate cancer cell | 39.7 ± 1.3 |
| Esophageal cancer cell | 35.5 ± 1.1 |
| Sarcoma cell | 45.5 ± 1.6 |
| Glioma cell | 58.8 ± 1.5 |
| Melanoma cell | 49.9 ± 2.0. |
| Lymphoma cell | 55.8 ± 1.7 |
| Bladder cancer cell | 55.2 ± 1.0 |

As shown in FIGS. 12(a), 12(b) and Table 6, the inventive long acting curcumin derivatives inhibited all of these 14 types of cells significantly. The inhibitory rates for all of these cell types were above 35.5%, among which the inhibitory rate for renal cancer cells was the highest, i.e. 60.6%.

Examples for utilizing the long acting curcumin derivatives to prepare any pharmaceutically acceptable dosage forms are shown as follows.

Example 1

Long acting curcumin was prepared by chemical synthesis, and a solvent was added. The mixture was then formulated into ampules conventionally.

Method and dosage for use: intramuscular injection of 100-500 mg long acting curcumin every 3-7 days.

Example 2

Long acting curcumin was prepared by chemical synthesis, and an excipient cyclodextrin was added. The mixture was then formulated into tablets or granules conventionally.

Method and dosage for use: oral administration of 100-500 mg long acting curcumin every 3-7 days.

Example 3

Long acting curcumin was prepared according to above Example methods, and water and an appropriate amount of solubilizer such as a polyethylene glycol solution were added. The mixture was then formulated into oral liquid solution (20 mg/ml) conventionally.

Method and dosage for use: oral administration of 100-500 ml long acting curcumin every 3-7 days.

Example 4

Long acting curcumin was prepared according to above Example methods, and then formulated into long acting curcumin capsules (20 mg/capsule) with the selected soft capsule materials including gelatin and sorbitol.

Method and dosage for use: oral administration of 100-500 mg long acting curcumin every 3-7 days.

Examples for utilizing the long acting curcumin derivatives to prepare food, beverage or health care products are shown as follows.

Example 5

To 50 kg flour, 1-5 g of long acting curcumin and an appropriate amount of nutriment and additives were added. The mixture was then made into noodles or crackers with an anti-depression or antitumor function.

Example 6

To 50 kg pure water, 1-5 g of long acting curcumin and an appropriate amount of orange juice, pineapple, or mango and additives were added. The mixture was then made into soft drinks with an anti-depression or antitumor function.

Example 7

To 1 g concentrated calcium tablets and 1 ml oral liquid, 10-50 mg of long acting curcumin was added. The mixture was then made into health care products with an anti-depression or antitumor function.

The above disclosure only relates to the preferable Examples of the invention, and are not intended to restrict the invention in any way. Any one skilled in the art, without departing from the scope of the technical solutions in the invention, can make equivalent Examples with some variations or modifications. However, any simple variations, equivalents and modifications made according to the technical spirit of the invention will still belong to the scope of the invention.

INDUSTRIAL APPLICABILITY

The inventive long acting curcumin derivatives are esters generated from the esterification reaction of cuminoids, and has a better slow-release effect than cuminoids itself. As a result, the in vivo bioavailability and medicine activity of curcumin are improved dramatically, thus rendering it be of a higher value in medical application. Just like the cuminoids in the prior art, the inventive curcumin derivative has a very broad application in the medical field. For example, it can be used for treating depression, cancer, hepatic fibrosis, or chronical renal failure, etc.

The invention claimed is:

1. A long acting curcumin derivative, wherein the long acting curcumin derivative has the following structural formula:

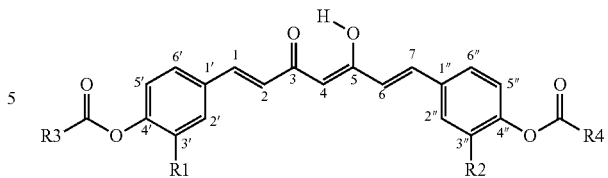

wherein:
R1 and R2 are hydrogen or methoxyl; and
R3 and R4 are each nonyl.

2. A method of treating depression in a subject comprising administering a long acting curcumin derivative according to claim 1 to said subject.

3. The method according to claim 2, wherein said long acting curcumin derivative comprises a pharmaceutically acceptable carrier and is in a formulation selected from the group consisting of a powder, tablet, pellet, capsule, micro-capsule, granule and a liquid derivative.

4. The method according to claim 2, wherein a long acting curcumin derivative is in a formulation selected from the group consisting of a beverage, food, food additive and health care product.

5. The method of claim 3, wherein said pharmaceutically acceptable carrier comprises an excipient, additive or flavor.

6. A method of treating a tumor in a subject comprising administering the long acting curcumin derivative according to claim 1 to said subject wherein the tumor is selected from the group consisting of leukaemia, cervical cancer, renal cancer, breast cancer, gastric cancer, colonic cancer, lung cancer cells, liver cancer, prostate cancer, esophageal cancer, myeloma, glioma, melanoma, lymphoma, bladder cancer, adenocarcinoma, ovarian cancer and skin cancer.

7. The method according to claim 6, wherein said long acting curcumin derivative comprises a pharmaceutically acceptable carrier in a formulation selected from the group consisting of a powder, tablet, pellet, capsule, micro-capsule, granule and a liquid derivative.

8. The method according to claim 6, wherein said long acting curcumin derivative is in a formulation selected from the group consisting of an antitumor beverage, food, food additives and health care product.

9. The method of claim 7, wherein said pharmaceutically acceptable carrier comprises an excipient, additive or flavor.

* * * * *